(12) United States Patent
Meruva et al.

(10) Patent No.: US 6,689,272 B2
(45) Date of Patent: Feb. 10, 2004

(54) ACETATE DETECTING SENSOR

(75) Inventors: Ravi Kumar Meruva, Burlington, MA (US); Jeffrey Chen-Yie Chien, Wellesley, MA (US); Chung Chang Young, Weston, MA (US)

(73) Assignee: Nova Biomedical Corporation, Waltham, MA (US)

( * ) Notice: Subject to any disclaimer, the term of this patent is extended or adjusted under 35 U.S.C. 154(b) by 285 days.

(21) Appl. No.: 09/836,403

(22) Filed: Apr. 17, 2001

(65) Prior Publication Data

US 2003/0010654 A1 Jan. 16, 2003

(51) Int. Cl.[7] .............................................. G01N 27/404
(52) U.S. Cl. ...................... 205/787; 204/415; 205/782.5
(58) Field of Search ................................ 204/415, 431, 204/432; 205/782.5, 783, 787

(56) References Cited

U.S. PATENT DOCUMENTS

| 2,913,386 A | * | 11/1959 | Clark |
| 4,495,051 A | * | 1/1985 | Fujita et al. |
| 4,659,434 A | * | 4/1987 | Driscoll et al. |
| 5,770,028 A | | 6/1998 | Maley et al. |

FOREIGN PATENT DOCUMENTS

| EP | 0 415 983 B1 | 3/1991 |
| EP | 0 316 380 B1 | 9/1991 |
| JP | 03188366 A | 8/1991 |

OTHER PUBLICATIONS

Riley, M., Chapter 1, Ion–Selective Electrode Methodology, CRC Press, 1979, pp. 1–21.
Bailey, P. L. et al., Perfomance Characteristics of Gas–sensing Membrane Probes, The Analyst, vol. 100, No. 1188, Mar. 1975, pp. 145–156.
Midgley, D. et al., The Determination of Ammonia in Condensed Steam and Boiler Feed–water with a Potentiometric Ammonia Probe, Analyst, vol. 97, Aug. 1972, pp. 626–633.
Midgley, D., Investigations into the Use of Gas–sensing Membrane Electrodes for the Determination of Carbon Dioxide in Power Station Waters, Analyst, vol. 100, Jun. 1975, pp. 386–399.
Forman, Lawrence W. et al., On–line monitoring and control of fermentation processes by flow–injection analysis, Analytica Chimica Acta, vol. 249, 1991, pp. 101–111.
Ross, J. W. et al., Potentiometric Gas Sensing Electrodes, Pure & Applied Chemistry, 35, 1973, pp. 473–487.

* cited by examiner

*Primary Examiner*—T. Tung
(74) *Attorney, Agent, or Firm*—Robert A. Deleault, Esq.; Mesmer & Deleault, PLLC

(57) ABSTRACT

An electrochemical sensor for detecting the presence and amount of acetate in cell culture and fermentation media. The electrochemical sensor has a pH electrode, an internal reference electrode, a special high-tensile strength gas permeable membrane, and internal reference electrolyte such that acetate concentration can be measured using a pretreatment buffer having a pH of about 5.5.

16 Claims, 4 Drawing Sheets

ACETATE DETECTING SENSOR

BACKGROUND OF THE INVENTION

1. Field of the Invention

The present invention relates to electrochemical sensors. Particularly, the present invention relates to an electrochemical sensor that is used to detect a species having a measurable vapor pressure over a sample solution by using an appropriate gas permeable membrane through which vapors diffuse. More particularly, this invention relates to an electrochemical sensor for detecting acetate in cell culture and fermentation media.

2. Description of the Prior Art

The concept of determining the partial pressure of a gas dissolved in a sample by measuring the pH of a thin film of solution separated from the sample by a gas permeable membrane was first described by Stow et al. in 1957. Thereafter, Severinghaus and Bradley constructed a probe that could measure the partial pressure of carbon dioxide ($CO_2$) in blood. In 1973, Ross et al. described several gas sensing electrodes responding to carbon dioxide, ammonia, amines, sulfur dioxide, nitrogen dioxide, hydrogen sulfide, hydrogen cyanide, hydrogen fluoride, acetic acid, and chlorine along with their mode of operation.

Analytes of interest in the fermentation process include nutrients (e.g. glucose, glutamine), metabolites (e.g. acetate, lactate), gene regulators (e.g. phosphate, oxygen, indoleacrylic acid) and desired products (e.g. antibiotics, recombinant proteins). Many difficulties arise when analyzing fermentation media due to the fact that fermentation media are a mixture of changing concentrations of proteins, metabolites, nutrients and cells. Acetic acid is a by-product of *E. coli* cultures grown on glucose either in the presence of high substrate concentration or when the level of dissolved oxygen is low. Low cell yield and reduced productivity are both associated with high concentrations of acetate.

Currently, acetate is measured using several analytical methods including high-pressure liquid chromatography (HPLC), enzymatic determination and colorimetry. In colorimetry, acetate is measured by converting acetate into acetic acid and using a pH dye that undergoes color change associated with the concentration level of acetate. This is achieved by using a membrane that separates two streams from one another. On one side of the membrane is an acid donor stream containing the sample and on the other side of the membrane is a neutral receiving stream containing an acid-base indicator. The acetic acid vapors diffuse through the membrane and dissolve in the neutral receiving stream. This causes a pH drop and a color change that can be detected by absorbance at 560 nanometers. In enzymatic determination, acetate kinase is used along with the coenzyme nicotinamide adenine dinucleotide (NADH). The measurement in this analytical method is based on a change in the absorbance at 340 nanometers of the coenzyme NADH.

In "Potentiometric Gas Sensing Electrodes," Ross et al., *Pure & Applied Chemistry*, Vol. 35, 1973, Page 473-ff, Ross et al. illustrated that it is feasible for an acetate sensor to be based on diffusion of acetic acid through a porous, gas permeable membrane. The principle used by Ross et al. is the basic Severinghaus electrode ($CO_2$) with a different internal electrolyte and membrane material. Membrane materials used by Ross et al. are cellulose acetate, Teflon, polyvinyl chloride, polyvinyl fluoride, polypropylene, and polyethylene. A disadvantage of the Ross sensor is that the samples must be adjusted to a pH less than two. At this low pH level, interference from acidic gases such as hydrogen fluoride (HF), sulfur dioxide ($SO_2$), formate and carbon dioxide occurs. This is so because these acidic gases, being smaller in size, have higher permeability coefficients than acetic acid. In fact, at pH 2.6 they have selectivity coefficients of more than one, thus, making the measurements of acetate concentration in fermentation impractical. The $pK_a$ of formic acid and hydrofluoric acid is 3.75 and 3.45 respectively. Consequently, despite Ross et al. suggestion, no usable and practical acetate sensors have been made for measuring cell and fermentation media.

Another problem with the prior art sensors is that they are not economical. The prior art sensors cost approximately four dollars per test not including the cost of labor to perform the test.

Therefore, what is needed is an electrochemical sensor that can detect acetate in cell culture and fermentation media. What is further needed is an acetate detecting electrochemical sensor that has a special membrane that allows for fast response time. What is still further needed is an acetate detecting electrochemical sensor that can detect sample acetate concentration when the sample is pretreated to a pH of 5.5 instead of a pH less than two. What is yet further needed is an acetate detecting electrochemical sensor with a buffer system for pretreatment of a sample that will allow for a measurable percentage of acetate to be converted into acetic acid while minimizing the effects of interfering species. What is still further needed is an acetate detecting electrochemical sensor that is more economical to use.

SUMMARY OF THE INVENTION

It is an object of the present invention to provide an electrochemical sensor that can detect acetate in cell culture and fermentation media. It is a further object of the present invention to provide an acetate detecting electrochemical sensor that has an acetic acid gas permeable membrane that allows for fast response time. It is still a further object of the present invention to provide an acetate detecting electrochemical sensor that can measure acetate concentrations within a sample when the sample is pretreated to a pH of 5.5 instead of pretreating to a pH of 2 or lower. It is yet a further object of the present invention to provide a buffer system for sample pretreatment that will allow for a measurable percentage of acetate to be converted into acetic acid while minimizing the conversion of interfering species. It is still a further object of the present invention to provide an acetate detecting electrochemical sensor that reduces the cost per test for measuring acetate concentrations in cell culture and fermentation media.

The present invention achieves these and other objectives by providing an electrochemical sensor for detecting acetate in cell culture and fermentation media. The sensor includes a pH glass electrode, an internal reference electrode, an internal reference filling solution capable of undergoing a reversible pH reaction in the presence of acetic acid, and an acetic acid gas permeable membrane.

The present invention is an acetate sensor that is based on a glass electrode with a pH sensitive tip. The glass pH electrode in combination with a reference electrode forms a complete electrochemical cell, whose e.m.f. is a function of the activity of the determinant gas in the sample. The pH sensitive tip is held against the gas permeable hydrophobic membrane so as to trap a thin film of the internal reference filling solution between the pH sensitive tip and the membrane. When the sensor is placed in a sample of determinant gas, the determinant gas diffuses through the membrane until the partial pressure of the gas in the thin film of electrolyte is equal to that in the sample. This equilibrium partial pressure of the determinant gas determines the pH of the thin film, which is measured by the glass pH electrode. For the acetate sensor, the pH of the thin film is directly proportional to the concentration of acetate in the sample.

The two basic components of the acetate sensor are an acetic acid gas permeable, hydrophobic membrane and a pH electrode. The sample is pre-treated with a buffer that maintains the sample at pH 5.5. This pretreatment of the sample to pH 5.5 is done to convert a fraction of the acetate into acetic acid and to reduce interference from formate, chloride and fluoride. At pH of 5.5, approximately fourteen percent of the acetate in the sample is converted into acetic acid. The acetic acid has a measurable vapor pressure over a sample solution so it diffuses through the membrane and dissolves in the thin film of internal reference filling solution trapped between the membrane and the pH electrode. The dissolution of the acetic acid in the internal reference filling solution causes a pH change, which is measured by the pH electrode. The magnitude of the pH change in the internal reference filling solution is a function of total acetate content in the sample.

The pH of the buffer solution resulting from the mixture of weak acid (HA) like acetic acid and its anion (A⁻) like sodium acetate is determined by the Henderson-Hasselbalch equation:

$$pH = pK_a + \log\frac{C_{A^-}}{C_{HA}} \quad \text{Eq. 1}$$

Where $K_a$=the dissociation constant of the acid.

$C_{A^-}$=the concentration of the anion; and $C_{HA}$=the concentration of the weak acid.

Because the $pK_a$ of acetic acid is constant at 4.74 and the $C_{A^-}$ is held constant in the internal reference filling solution, the pH of the internal reference filling solution can be related to $C_{HA}$ as shown in the following equation:

$$pH = K - \log C_{HA} \quad \text{Eq. 2}$$

where K is defined as:

$$K = pK_a + \log C_{A^-} \quad \text{Eq. 3}$$

Measurement of the pH of the internal reference filling solution and relating that to the concentration of acetate in the sample forms the basis for the acetate determination.

The present invention has the advantage of pretreating samples to a pH 5.5. Prior to the present invention, samples had to be adjusted to a pH of 2 or lower to completely convert the acetate to acetic acid in sufficient quantity to provide a sufficient amount of diffusable gas for measurement. At this pH level, prior art sensors are not usable as acetate detecting sensors because of interference from acidic gases. At a pH of 5.5, approximately 14 percent of the acetate in the sample will be converted into acetic acid. This provides a good balance of acetate/acetic acid conversion to electrode sensitivity and selectivity to provide a reliable acetate detecting sensor when combined with the special membrane of the present invention.

Additional advantages and embodiments of the present invention will be set forth in part in the detailed description that follows, and in part will be apparent from the description, or may be learned by practice of the invention.

It is understood that the foregoing general description and the following detailed description are exemplary and explanatory and are intended to provide further explanation of the invention as claimed.

DETAILED DESCRIPTION OF THE PREFERRED EMBODIMENT

Figure 1:
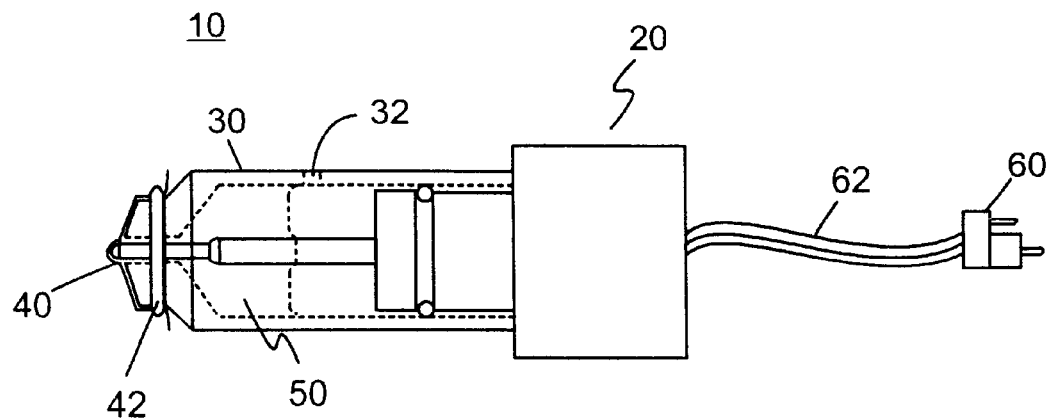
FIG. 1 is a side view of the present invention showing the acetate electrode assembled for measuring acetate.

The preferred embodiment of the present invention is illustrated in FIGS. 1–8. FIG. 1 shows an acetate sensor 10 of the present invention. Sensor 10 has an electrode system 20, a housing 30, a vent hole 32 through the wall of housing 30, a membrane 40 secured to one end of housing 30, an internal reference filling solution 50, a sensor cable 62, and a sensor connector 60.

Figure 2:
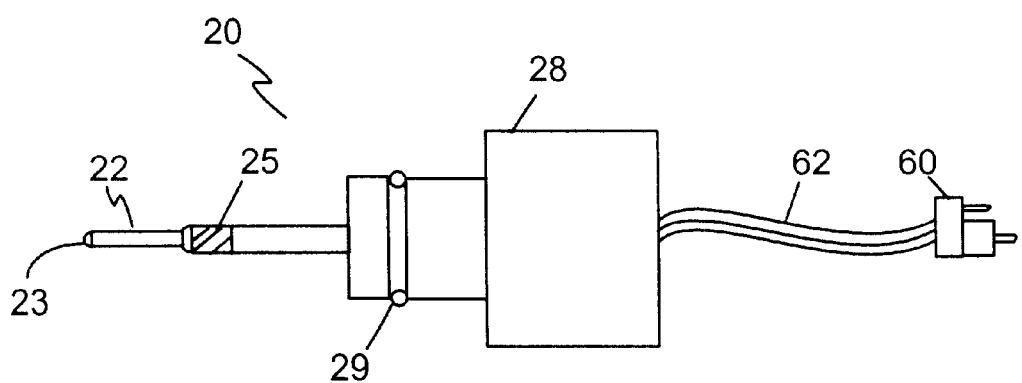
FIG. 2 is a cross-sectional view of the electrode system of the present invention showing the pH-measuring electrode, the reference electrode and the electrode body.

Turning now to FIG. 2, electrode system 20 includes a measuring electrode 22, a reference electrode 25 and an electrode body 28. Measuring electrode 22 is a glass pH electrode where only a tip portion 23 of measuring electrode 22 is pH sensitive and the remaining portion is made of an insulating material, preferably an insulating glass that does not respond to changes in pH. Reference electrode 25 is located a predetermined distance from tip portion 23 such that reference electrode 25 is within the internal reference filling solution 50 when assemble to housing 30, as shown in FIG. 1. Reference electrode 25 provides a stable potential within the internal reference filling solution 50 against which the potential of measuring electrode 22 is compared. Any reference electrode 25 that is known to those skilled in the art as having the required characteristics of a reference electrode can be used in the present invention. In the present invention, reference electrode 25 is preferably a silver/silver chloride electrode.

Tip portion 23 is about 2 mm in diameter. Tip portion 23 of measuring electrode 22 may be either flat, hemispherical or convex shaped. In the present invention, the hemispherical shape is used. The membrane material selected for membrane 30 along with the diameter of measuring electrode 22 and shape of tip portion 23 is important for optimizing the useful life of sensor 10. This is so because tip portion 23 of measuring electrode 22 stretches membrane 30 attached to housing 40. Measuring electrode 22 and reference electrode 25 are secured within electrode body 28 generally with adhesives. Electrode body 28 is made of any plastic material, preferable polyvinyl chloride (PVC). Electrode body 28 may be made as a single, unitary piece or a multi-piece component. A connecting cable 62 is electrically coupled to measuring electrode 22 and reference electrode 25. Connecting cable 62 may be a coaxial cable where measuring electrode 22 is coupled to the center conductor and reference electrode 25 is coupled to the outer shield. Connecting cable 62 may also be a pair of individual, single or multi-strand, conductor-type connecting cables. To facilitate connecting the acetate sensor 10 to a measuring system, a connector 60 may be used. Surrounding electrode body 28 is an O-ring 29. O-ring 29 is sized to provide a frictional fit of electrode body 28 within membrane housing 30.

Figure 3:
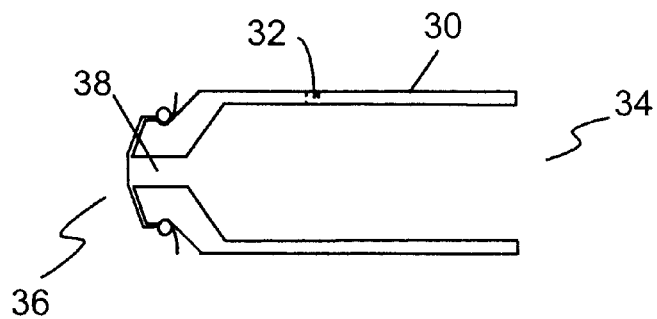
FIG. 3 is a cross-sectional view of the membrane housing of the present invention.

Turning now to FIG. 3, housing 30 has a tubular shape with an electrode receiving end 34 and a membrane end 36. Electrode receiving end 34 is adapted to slidably receive electrode system 20. Membrane end 36 has an aperture 38 in the center for accommodating measuring electrode 22. Housing 30 is slidably attached to electrode body 28 by way of an O-ring 29 as shown in FIG. 2. Housing 30 may also have threads (not shown) that allows housing 30 to be screwed onto mating threads (not shown) located on electrode body 28. Housing 30 is made of a plastic material, preferably a transparent or semi-transparent acrylic material. Housing 30 includes a pressure relief mechanism that can exist in several different forms. It can be a groove in either the inside wall of housing 30 or along electrode body 28, or a vent hole may be formed in the sidewall of housing 30. In the preferred embodiment of the present invention, the pressure relief mechanism is a vent hole 32 as shown in FIG. 3.

Reference filling solution 50 is enclosed in housing 40. Reference filling solution 50 is an electrolyte solution in which the substance that is being measured participates in an equilibrium reaction involving an ion that can be indirectly measured by measuring electrode 22. An example of a preferred composition of the internal filling solution 50 in the present invention for measuring acetate concentration in a sample is 140 millimole (mM) sodium chloride and 50 mM sodium acetate.

Membrane 40 is a micro-porous membrane that is an inert, porous, polymeric matrix that acts as a support having a plurality of voids through which the determinant gas diffuses. A film of air is retained in the pores of the membrane. To operate as a usable membrane, it was found that the material should have a porosity of about seventy percent and a pore size of less than one micron. The thickness of the membrane is preferably about 100 microns. Because membrane 40 is stretched by measuring electrode 22 when sensor 10 is assembled, membrane 40 must have sufficient tensile strength so that it can withstand the stretching caused by protruding tip portion 23 and remain in this stretched condition without tearing. Unexpectedly, it was found that the best material for use as membrane 40 is a polyvinylidenefluoride (PVF) membrane. It has the required tensile strength and gas permeability for use as an acetate membrane in the present invention. PVF is inert, is a high purity polymer that has high tensile strength, and is hydrophobic. Various PVF membranes having different pore sizes (0.1 micron and 0.2 micron) were tested as well as membranes made of polypropylene (brand name Metricel manufactured by Gelman) and polytetrafluoroethylene (brand name TF-200 and TF-450 manufactured by Gelman). The preferred PVF membrane is a membrane material manufactured by Millipore and sold under the trademark Durapel. It has a pore size of 0.2 microns and a thickness of about 100 microns. The Metricel, TF-200 and TF-450 lacked the necessary tensile strength and tore apart when stretched by measuring electrode 22. The only polytetrafluoroethylene membrane that provided satisfactory results is a membrane sold under the brand name of Pore-Tex manufactured by DeWal Industries.

To assemble acetate sensor 10, membrane 40 is attached to membrane end 36 of housing 30 using an O-ring 42. Housing 30 is filled with internal reference filling solution 50 up to vent 32, being careful not to trap any air bubbles along aperture 38 or against membrane 40. Electrode system 20 is inserted into electrode receiving end 42 of housing 40. Tip portion 23 is forced against membrane 40 until membrane housing 30 is fully assembled onto electrode body 28. O-ring 29 on electrode body 28 creates a tight fit between membrane housing 30 and electrode body 28. Tip portion 23 stretches membrane 40, creating a thin layer of reference filling solution 50 between membrane 40 and measuring electrode 22. When fully assembled, tip portion 23 extends through aperture 38 and beyond membrane end 36 of housing 30. Vent 32 allows for air and excess internal reference filling solution 50 to escape, thus relieving any pressure buildup caused by inserting electrode system 20 into housing 30. Using this pressure release mechanism prevents additional stretching of flexible membrane 40 caused by hydrostatic pressure buildup in addition to the stretching caused by measuring electrode 22. Failure to use an adequate pressure release mechanism would cause more of the internal reference filling solution 50 to be located between tip portion 23 and membrane 30. This would cause acetate sensor 10 to have a very slow response. Membrane end 36 of housing 30 is exposed to the sample so that tip portion 23 comes into contact with the sample. Acetate ions upon being treated with acid forms acetic acid gas, which diffuses through membrane 40 and into the thin film of internal reference filling solution 50 between tip portion 23 and membrane 40. The diffusion of acetic acid gas into the thin film causes a change in pH in the thin film that is detected by measuring electrode 22.

Figure 4:
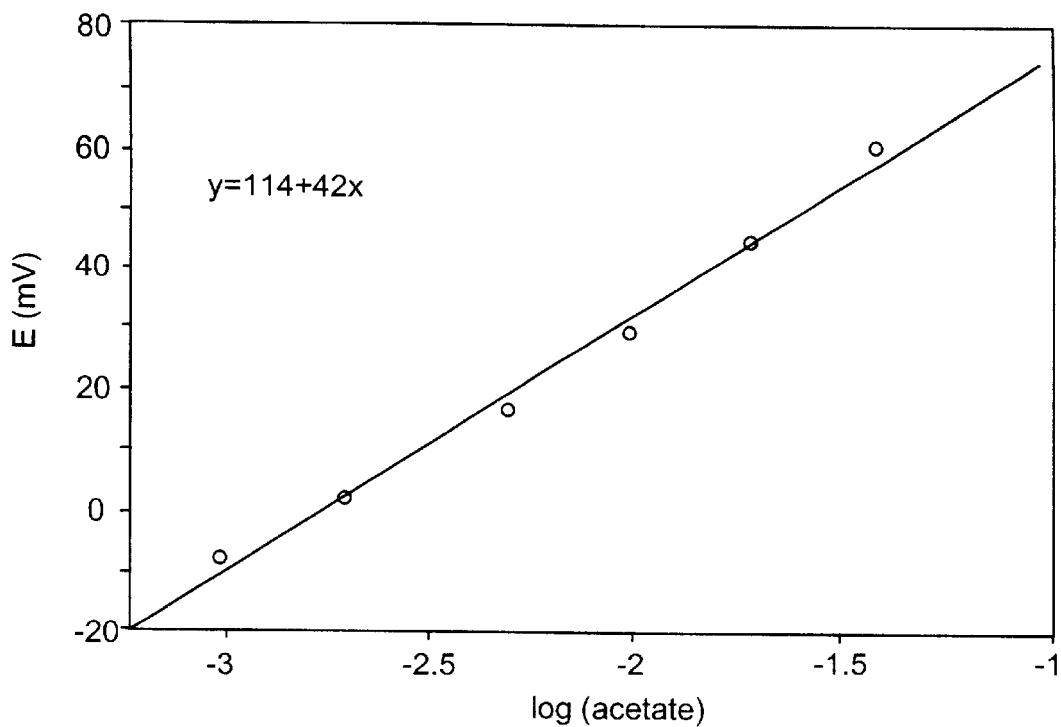
FIG. 4 is an illustration of a typical calibration graph for the present invention measured over a predetermined acetate concentration range.

The response of a sensor of the present invention was studied using a Nova CRT 16 analyzer. The sensor cap and connectors were configured for use in the Nova CRT 16 analyzer. The sensor was calibrated using two different standard solutions. Standard A solution contained a 5.0 mM acetate ion concentration and standard B contained a 20 mM acetate ion concentration. A 100 mM morpholinoethanesulfonic acid (MES) buffer, pH 5.5, was used as a diluent as well as the acid to convert the acetate into acetic acid. FIG. 4 shows the typical calibration plot, EMF v. log (acetate concentration), for an acetate sensor. The concentration range for the calibration is 1.0 mM to 40.0 mM acetate ions. Thirty (30) seconds after sample treatment and after bringing the sample and sensor into contact with each other, the sensor readings are recorded. The calibration slope of the acetate sensor obtained when 30-second readings are used is approximately 42 mV/decade for every ten-fold change in acetate concentration. The slope of the electrode is calculated using the following equations.

$$S = \frac{E_{StdB} - E_{StdA}}{\log\frac{B}{A}} \qquad \text{Eq. 4}$$

where:
  B is the acetate activity in Standard B; and
  A is the acetate activity in Standard A By further modifications, it can be shown that the unknown activity of the acetate in a sample solution can be calculated from the following equation.

$$A_x = A \times 10^{\left(\frac{E_x - E_A}{S}\right)} \qquad \text{Eq. 5}$$

where:

$E_x$ is the potential of the sample solution

The Nernstian slope of 59.2 mV/decade can be obtained if the data is recorded after complete equilibration of the acetic acid in the sample and in the thin layer trapped between the membrane 40 and the measuring electrode 22.

The stability of the sensor of the present invention was evaluated by measuring the drift rates of the absolute potential over a period of two weeks. Besides the drift attributed to the pH electrode, drift can also result from osmotic pressure differences. For example, if the concentrations of dissolved species in the solution on the two sides of the membrane are different, there will be a difference in osmotic pressure. Water vapor will diffuse through the membrane until the activity of water is the same on each side of the membrane. The transfer of water vapor across the membrane results in either dilution or concentration of the internal electrolyte in the thin film. Water vapor transfer will cause the acetate sensor's e.m.f. to drift. The rate of drift depends on water transfer across hydrophobic membrane 40, which is determined by the osmotic pressure and also the permeability of water vapor. The osmotic effects cannot be completely eliminated but the effects can be minimized by matching the osmotic strengths of the sample and the internal electrolyte. This can be accomplished by diluting the sample solutions to desired levels, by selecting appropriate concentrations for the sample pretreatment reagents, or by adjusting the osmotic strength of the internal filling solution.

Figure 5:
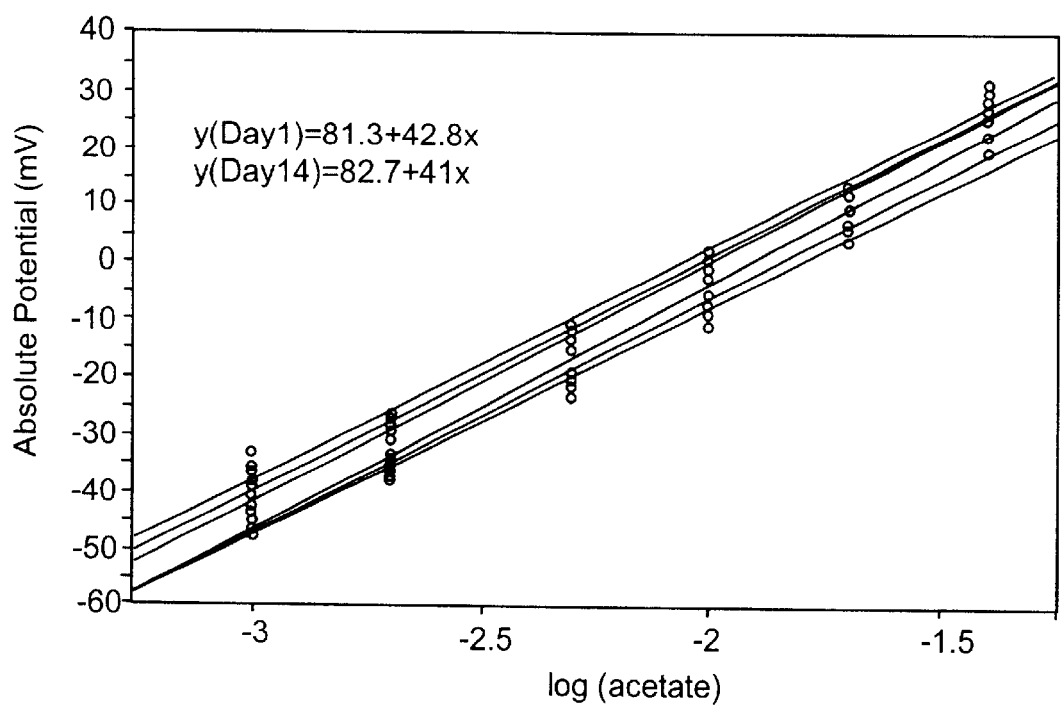
FIG. 5 is a graphical illustration showing the absolute potential drift observed in the present invention over a period time.

As seen in FIG. 5, the present invention shows stability in terms of absolute potential drift. The present invention shows an absolute potential drift of about 0.75 mV/decade for every ten-fold change in concentration of acetate. The slope of the sensor varied with a standard deviation of approximately +/−0.5 units as shown in FIG. 5.

Table 1 below shows the precision and accuracy of measuring acetate from 1 mM to 40 mM in the buffered sample solution over a period of three weeks. Except at a low concentration of 1 mM acetate in the buffered sample solution, the acetate sensor measures acetate in the sample solution with a day-to-day coefficient of variation (CV) in the range of about 3 percent.

TABLE 1

| | Day-to-Day Performance | | | | | |
|---|---|---|---|---|---|---|
| | 1 mM | 2 mM | 5 mM | 10 mM | 20 mM | 40 mM |
| Day 1 | 0.97 | 1.79 | 4.07 | 8.74 | 19.16 | 42.58 |
| Day 2 | 0.98 | 1.74 | 4.07 | 8.64 | 19.36 | 44.1 |
| Day 3 | 1.07 | 1.73 | 4.13 | 8.82 | 18.64 | 42.6 |
| Day 4 | 1.00 | 1.71 | 4.16 | 8.98 | 18.63 | 42.91 |
| Day 6 | 1.02 | 1.78 | 4.3 | 9.34 | 19.73 | 44.65 |
| Day 7 | 1.08 | 1.75 | 4.25 | 9.2 | 19.64 | 44.55 |
| Day 8 | 0.99 | 1.74 | 4.24 | 9.34 | 20.25 | 45.62 |
| Day 10 | 1.05 | 1.80 | 4.32 | 9.45 | 20.54 | 46.24 |
| Day 14 | 0.95 | 1.76 | 4.18 | 8.94 | 19.2 | 44.33 |
| Day 20 | 0.98 | 1.82 | 4.32 | 9.2 | 19.87 | 45.87 |
| Ave. | 1.01 | 1.76 | 4.20 | 9.07 | 19.50 | 44.35 |
| sd | 0.04 | 0.03 | 0.10 | 0.28 | 0.63 | 1.33 |
| cv % | 4.39 | 1.96 | 2.29 | 3.09 | 3.23 | 3.00 |

The lower limit of the response range is determined by the concentration of the determinant gas in the internal reference filling solution. The pH of the thin film solution between the membrane and the measuring electrode can not be higher than the pH of the internal filling solution. Thus, the limit of detection is represented by the concentration of acetic acid in the thin film when equilibrium has been achieved between the acetic acid that is diffusing into the thin film from the internal reference filling solution and acetic acid diffusing out of the thin film into a sample that has no acetic acid.

The pH of the internal filling solution is about pH 7.5. The concentration of acetate in the internal filling solution is about 50 mM. Using the Henderson-Hasselbalch equation, and applying the $pK_a$ of acetic acid to be 4.74, the acetic acid concentration in the internal filling solution is determined to be about 0.086 mM. The practical determination of detection limits can be hampered by the long response time encountered at concentrations that are close to the detection limit. In the experiments performed, it was determined that the lower detection limit for the present invention was close to 0.5 mM and the upper detection limit was 200 mM. The present invention can achieve concentrations above 50 mM. However, at these higher concentrations, there is a chance for hysteresis to occur. The longer the present invention is exposed to the higher concentrations of determinant, the greater the amount of determinant that will diffuse into the internal filling solution. This will increase the subsequent recovery time before the present invention can give a correct response in a sample with a lower concentration of determinant.

Gas sensing probes, like the present invention, tend to exhibit faster response times at higher determinant species concentrations. The response time becomes slower as the lower limit of detection is approached. The factors that determine the response time of a sensor like the present invention are the internal filling solution composition, thickness of the thin film, membrane parameters and experimental conditions. The time that is required to reach 90 percent of the signal was determined to be 30 seconds in changing the concentration from 2 mM to 10 mM and 45 seconds in changing the concentration from 10 mM to 2 mM.

Gas sensing electrodes, like the present invention, demonstrate outstanding selectivity. They can only suffer direct interference from dissolved species in the sample which can both diffuse rapidly into the thin film and either change activity of the species detected by the sensor or interfere with the response of the measuring electrode. In the case of the present invention, which uses a pH electrode, any volatile species that can diffuse quickly from the sample into the thin film and also have acidity or basicity comparable or greater than that of the determinant species is going to cause interference.

In the pretreatment of the sample, the sample solution is mixed with acid solution to yield a solution with a pH of about 5.5. This pretreatment is done to ensure that all of the basic interferent gases like ammonia, hydrazine, methylamine, etc., are protonated and are no longer volatile to diffuse across the membrane. The interference expected is that from the acidic gases such as sulfur dioxide, carbon dioxide, nitrogen dioxide, formate and hydrogen fluoride. Carbon dioxide is one of the major chemical species found in cell culture and fermentation media.

Figure 6:
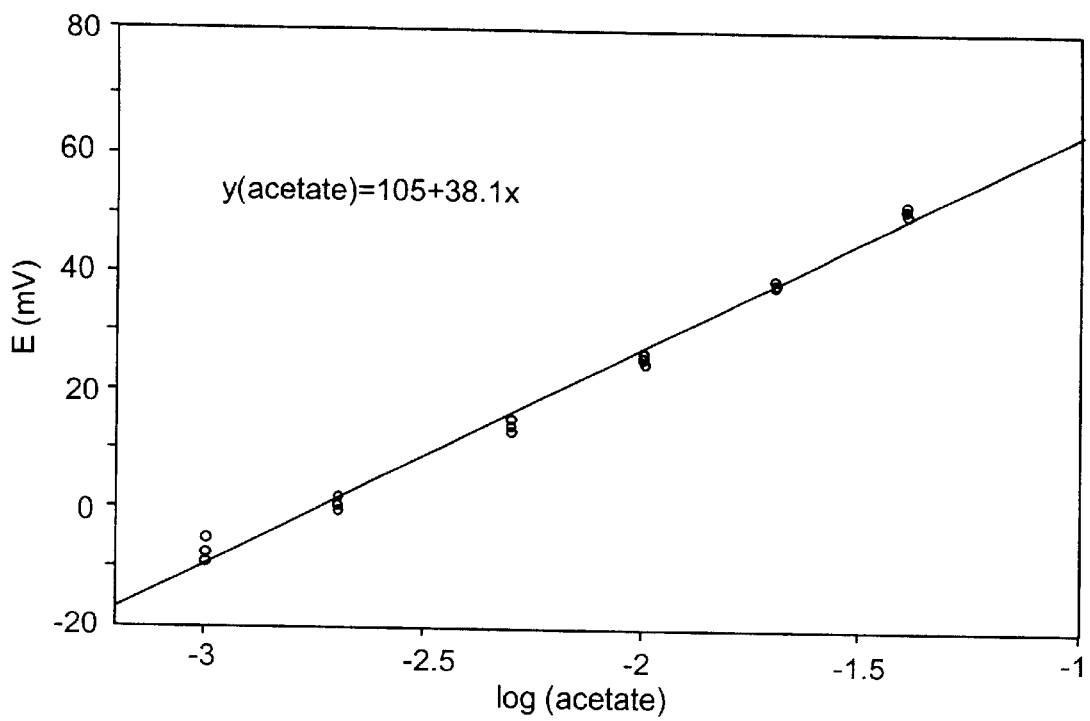
FIG. 6 is an illustration of the response of the present invention in the presence of bicarbonate.

The response of the present invention towards acetate in the presence of bicarbonate was recorded. FIG. 6 is a graphical illustration of this response. At each level of acetate from 1 mM to 40 mM, bicarbonate was varied from 1 mM to 40 mM. Except at low concentrations of acetate, as shown in FIG. 6, the bicarbonate has a negligible effect on the measurement of acetate in a sample.

Figure 7:
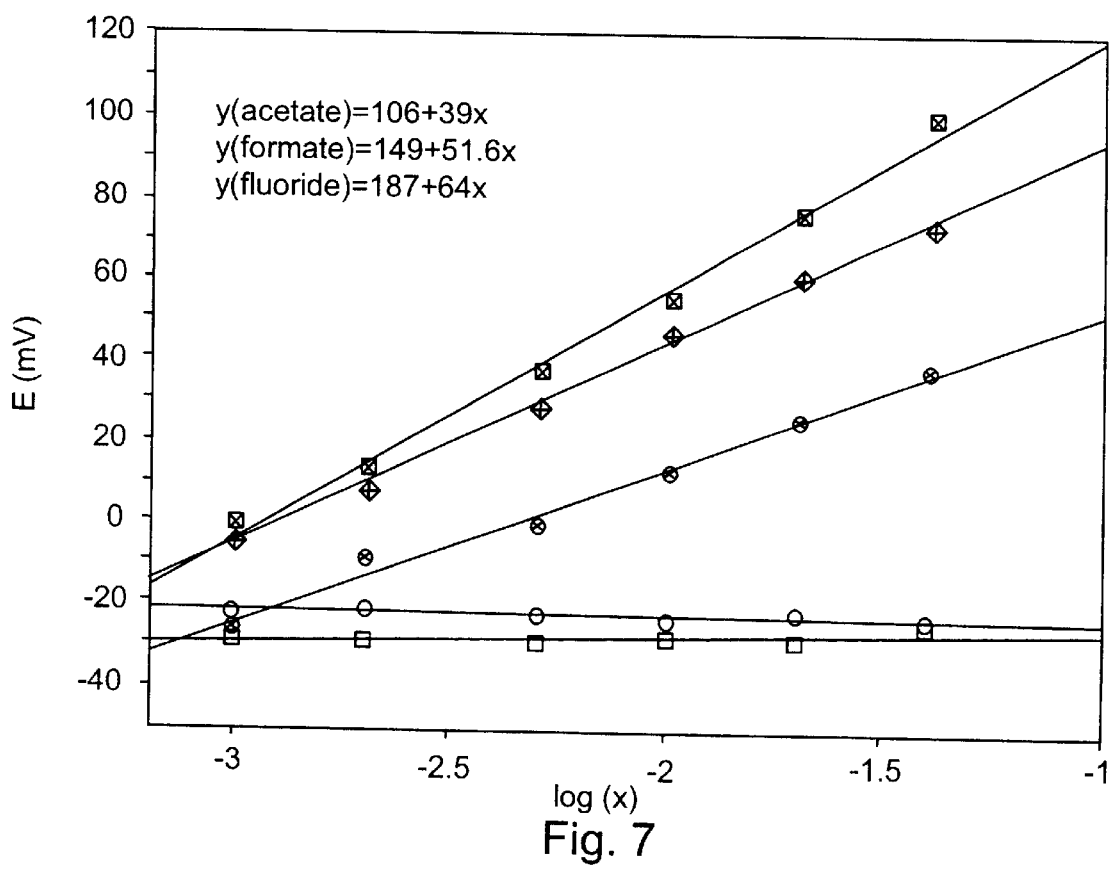
FIG. 7 is a graphical illustration of the response of the present invention in the presence of interferents at sample pH of 2.6.

Of all of the interferents tested, only formate and hydrogen fluoride were found to have a selectivity coefficient of more than one when the buffer used to convert salt into acid form had a pH of 2.6. Since both compounds are smaller than acetic acid they both have higher permeability coefficients than acetic acid. FIG. 7 illustrates the test results obtained when samples containing the respective determinants, i.e. acetate, formate, fluoride, etc., were treated with a pH 2.6 buffer. As illustrated, the sensor has greater sensitivity and selectivity to formate and fluoride than to acetate. Consequently, at this sample pH level, the sensor would not be useful as an acetate sensor for cell culture and fermentation media.

Figure 8:
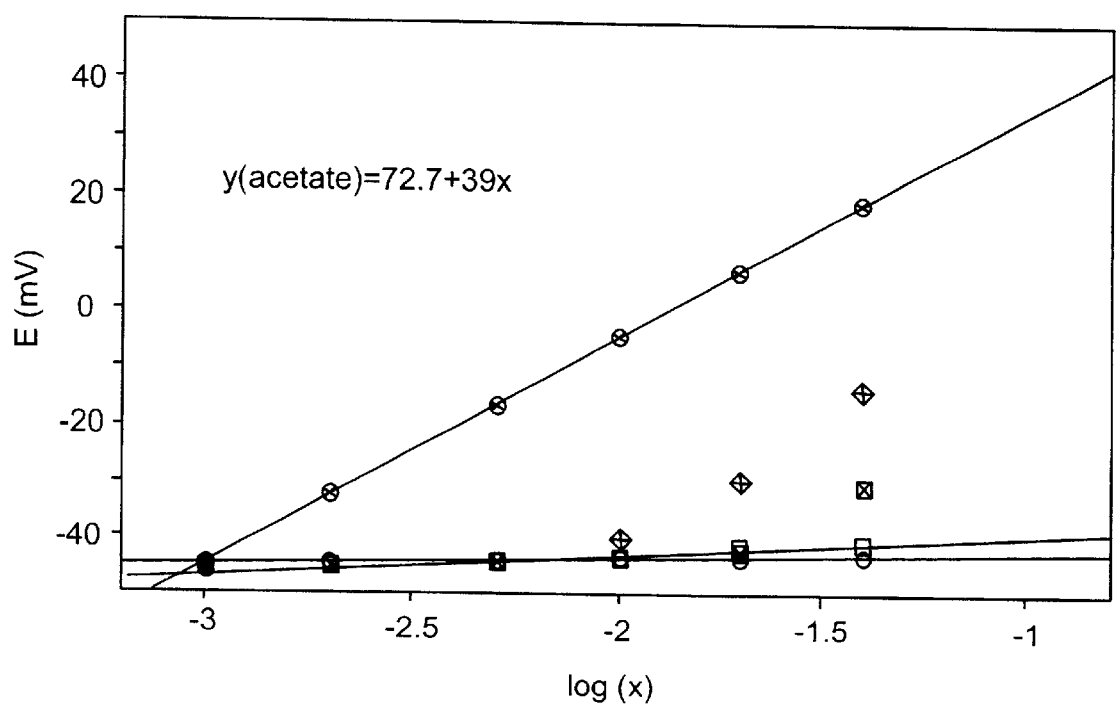
FIG. 8 is a graphical illustration of the response of the present invention in the presence of interferents at sample pH of 5.5.

MES buffer with a pH of 5.5 was considered as a buffering agent to reduce this problem. However, there were concerns that an insufficient amount of acetate/acetic acid conversion would exist to provide a meaningful quantity of acetic acid to provide sufficient sensor sensitivity. FIG. 8 illustrates the test results obtained when samples containing the respective determinants mentioned above were treated with a pH 5.5 MES buffer. Since the $pK_a$ of formic acid and hydrofluoric acid is 3.75 and 3.45 respectively, at pH 5.5 only 1.7 percent of the formate is converted into formic acid and only 0.88 percent of the hydrogen fluoride is converted into hydrofluoric acid. This considerably reduces the amount of interference arising from the high permeability constants of formic acid and hydrofluoric acid. As illustrated in FIG. 8, the use of a pH 5.5 MES buffer as the sample treatment buffer coupled with the high tensile strength membrane provides a sensor capable of measuring acetate concentration in cell cultures and fermentation media.

What is claimed is:

1. An acetate sensor for detecting the presence and amount of acetate in cell culture and fermentation media, said sensor comprising:
    a pH measuring electrode having a pH-sensitive tip portion;
    a housing having a membrane end and a measuring electrode receiving end;
    a polyvinylidenefluoride membrane attached to said membrane end of said housing; and
    a liquid electrolyte suitable for undergoing a reversible reaction with acetic acid gas within said housing and contacting said gas permeable membrane wherein said tip portion of said measuring electrode is in contact with said membrane forming a thin layer of said electrolyte therebetween; and
    wherein said acetate sensor is capable of detecting the presence and amount of acetate in a sample treated to a pH of about 5.

2. The sensor of claim 1 wherein said measuring electrode is a glass pH electrode.

3. The sensor of claim 1 wherein said electrolyte is a liquid mixture of sodium acetate and sodium chloride.

4. The sensor of claim 3 wherein said electrolyte has a concentration of about 140 mM of sodium chloride and about 50 mM of sodium acetate.

5. The sensor of claim 1 wherein said membrane has a porosity of about 70 percent.

6. The sensor of claim 5 wherein said membrane contains pores having a pore size of about 0.2 micron.

7. An acetate sensor kit comprising:
    a pH electrode system having a pH measuring electrode and a reference electrode;
    a membrane housing adapted for receiving said electrode system;
    at least one polyvinylidenefluoride membrane adapted for attaching to said membrane housing and for contacting said pH measuring electrode;
    a quantity of electrolyte solution adapted for adding a predetermined amount of said electrolyte solution to said housing having said at least one membrane attached thereto, said predetermined amount being sufficient to have liquid contact between said measuring electrode and said reference electrode; and
    wherein said acetate sensor kit forms an acetate sensor capable of detecting the presence and amount of acetate in a sample treated to a pH of about 5.

8. The kit of claim 7 wherein said at least one membrane has sufficient tensile strength to withstand a predetermined amount of stretching when said measuring electrode is mounted to said housing containing said membrane and said electrolyte solution.

9. The kit of claim 7 further comprising a quantity of buffer for treating said sample of cell culture or fermentation media.

10. The kit of claim 9 wherein said buffer has a pH of about 5.5.

11. The kit of claim 10 wherein said buffer is morpholinoethanesulfonic acid.

12. A method of measuring acetate concentration in cell culture and fermentation media using an acetate sensing electrode, said method comprising:
    treating a fluid sample containing an unknown acetate concentration with a pH 5.5 buffer; and
    measuring the partial pressure of acetic acid using an acetate sensing electrode having a polyvinylidenefluoride membrane.

13. The method of claim 12 further comprising correlating said partial pressure measurement of acetic acid to the concentration of acetate in said fluid sample.

14. The method of claim 12 wherein said treating step further includes treating said fluid sample with morpholinoethanesulfonic acid buffer.

15. A method of making an acetate measuring sensor capable of measuring a sample treated to about pH 5, said method comprising:
    attaching a polyvinylidenefluoride membrane to a gas sensing electrode membrane housing;
    filling said membrane housing with a predetermined amount of reference electrolyte configured for measuring acetic acid gas such that said electrolyte contacts said membrane; and
    inserting a gas sensing electrode system having a pH measuring electrode and a reference electrode into said membrane housing containing said electrolyte until said housing is fully seated onto said electrode system forming an acetate measuring sensor capable of detecting and measuring the amount of acetate in a sample treated to a pH of about 5.5.

16. The method of claim 15 wherein said filling step further includes removing any air bubbles trapped between said membrane and the exposed surface of said electrolyte before inserting said gas sensing electrode.

* * * * *